US011273430B2

(12) United States Patent
Wang et al.

(10) Patent No.: US 11,273,430 B2
(45) Date of Patent: Mar. 15, 2022

(54) OLEFIN AROMATIZATION CATALYST, PREPARATION METHOD AND USE THEREOF, AND LOW-CARBON OLEFIN AROMATIZATION PROCESS

(71) Applicants: China Energy Investment Corporation Limited, Beijing (CN); National Institute of Clean-and-Low-Carbon Energy, Beijing (CN)

(72) Inventors: Hui Wang, Beijing (CN); Lisa Nguyen, Beijing (CN); Junjun Shan, Beijing (CN); Joshua Miles, Beijing (CN); Jihong Cheng, Beijing (CN); Hua Liu, Beijing (CN)

(73) Assignees: China Energy Investment Corporation Limited, Beijing (CN); National Institute of Clean-and-Low-Carbon Energy, Beijing (CN)

(*) Notice: Subject to any disclaimer, the term of this patent is extended or adjusted under 35 U.S.C. 154(b) by 0 days.

(21) Appl. No.: 16/887,070

(22) Filed: May 29, 2020

(65) Prior Publication Data
US 2021/0016261 A1 Jan. 21, 2021

(30) Foreign Application Priority Data
Jul. 19, 2019 (CN) .......................... 201910654576.2

(51) Int. Cl.
*B01J 29/44* (2006.01)
*B01J 21/04* (2006.01)
(Continued)

(52) U.S. Cl.
CPC .............. *B01J 29/44* (2013.01); *B01J 21/04* (2013.01); *B01J 27/16* (2013.01); *B01J 29/042* (2013.01); *B01J 29/044* (2013.01); *B01J 29/045* (2013.01); *B01J 29/40* (2013.01); *B01J 29/405* (2013.01); *B01J 29/42* (2013.01); *B01J 29/46* (2013.01); *B01J 29/48* (2013.01); *B01J 29/83* (2013.01); *B01J 29/90* (2013.01); *B01J 37/0009* (2013.01); *B01J 37/0018* (2013.01); *B01J 37/0201* (2013.01); *B01J 37/04* (2013.01); *B01J 37/088* (2013.01); *B01J 37/10* (2013.01); *B01J 37/28* (2013.01); *B01J 38/02* (2013.01); *B01J 38/12* (2013.01); *C07C 2/42* (2013.01); *C07C 2/46* (2013.01); *C07C 15/04* (2013.01); *C07C 15/06* (2013.01); *C07C 15/08* (2013.01); *B01J 2229/186* (2013.01); *B01J 2229/20* (2013.01); *B01J 2229/37* (2013.01); *B01J 2229/42* (2013.01); *C07C 2521/04* (2013.01); *C07C 2527/18* (2013.01); *C07C 2529/06* (2013.01); *C07C 2529/064* (2013.01); *C07C 2529/068* (2013.01); *C07C 2529/072* (2013.01);
(Continued)

(58) Field of Classification Search
CPC ... B01J 38/02; B01J 38/12; B01J 21/04; B01J 27/16; B01J 29/044; B01J 29/042; B01J 29/045; B01J 29/405; B01J 29/40; B01J 29/44; B01J 29/46; B01J 29/48; B01J 29/42; B01J 29/83; B01J 29/90; B01J 2229/20; B01J 2229/37; B01J 2229/42; B01J 2229/186; B01J 37/0018; B01J 37/088; B01J 37/0009; B01J 37/04; B01J 37/0201; B01J 37/10; B01J 37/28; Y02P 20/52; C07C 2/42; C07C 2/76; C07C 15/04; C07C 15/06; C07C 15/08; C07C 2529/40; C07C 2529/42; C07C 2529/44; C07C 2529/46; C07C 2529/48; C07C 2529/06; C07C 2529/064; C07C 2529/068; C07C 2529/072; C07C 2529/076; C07C 2521/04; C07C 2527/18
USPC ........ 502/60, 61, 63, 64, 66, 69, 71, 73, 74; 585/400, 407, 415, 417, 418, 419, 420; 208/134, 135, 136, 137, 138, 139
See application file for complete search history.

(56) References Cited

U.S. PATENT DOCUMENTS 4,638,106 A * 1/1987 Pieters ..................... B01J 29/40
585/408
5,026,937 A 6/1991 Bricker
(Continued)

FOREIGN PATENT DOCUMENTS

CN 101596461 A 12/2009
CN 103282119 A 9/2013
(Continued)

OTHER PUBLICATIONS

Zhang, et al. "Development of Process and Catalyst of Low Olefin", Journal of Fushun Petroleum Institute, Jan. 2002. (Chinese text of the article and English Abstract Only).
(Continued)

*Primary Examiner* — Elizabeth D Wood
(74) *Attorney, Agent, or Firm* — Duane Morris LLP

(57) ABSTRACT

The present discloses an aromatization catalyst, preparation process and application thereof and a low-carbon olefin aromatization process. The aromatization catalyst comprises a microporous material, a binder and a modifier; the microporous material is a zeolite molecular sieve, the binder is alumina, the modifier is phosphorus, and the molar ratio of the aluminum element in the binder to the phosphorus element is more than or equal to 1 and less than 5; the ratio of the acidity of the strongly acidic sites to the acidity of the weakly acidic sites of the olefin aromatization catalyst is less than 1.

22 Claims, 3 Drawing Sheets

(51) Int. Cl.

| | | |
|---|---|---|
| *B01J 27/16* | (2006.01) | |
| *B01J 37/04* | (2006.01) | |
| *B01J 37/00* | (2006.01) | |
| *B01J 37/02* | (2006.01) | |
| *B01J 37/10* | (2006.01) | |
| *C07C 2/42* | (2006.01) | |
| *B01J 37/08* | (2006.01) | |
| *B01J 29/83* | (2006.01) | |
| *B01J 37/28* | (2006.01) | |
| *B01J 29/46* | (2006.01) | |
| *B01J 29/48* | (2006.01) | |
| *B01J 29/04* | (2006.01) | |
| *B01J 29/40* | (2006.01) | |
| *B01J 29/42* | (2006.01) | |
| *B01J 38/02* | (2006.01) | |
| *B01J 29/90* | (2006.01) | |
| *B01J 38/12* | (2006.01) | |
| *C07C 15/06* | (2006.01) | |
| *C07C 15/08* | (2006.01) | |
| *C07C 15/04* | (2006.01) | |
| *C07C 2/46* | (2006.01) | |

(52) U.S. Cl.
CPC .... *C07C 2529/076* (2013.01); *C07C 2529/40* (2013.01); *C07C 2529/42* (2013.01); *C07C 2529/44* (2013.01); *C07C 2529/46* (2013.01); *C07C 2529/48* (2013.01)

(56) References Cited

U.S. PATENT DOCUMENTS

| | | | |
|---|---|---|---|
| 6,355,591 B1 * | 3/2002 | Kuvettu | B01J 27/16 502/64 |
| 7,510,644 B2 * | 3/2009 | Overbeek | B01D 53/02 208/120.01 |
| 9,314,779 B2 * | 4/2016 | Ghosh | B01J 35/0006 |
| 9,815,047 B2 | 11/2017 | Yanagawa et al. | |
| 10,173,203 B2 * | 1/2019 | Iwasa | B01J 29/06 |
| 2005/0194289 A1 * | 9/2005 | Overbeek | C10G 29/205 208/120.01 |
| 2009/0209794 A1 | 8/2009 | Lauritzen et al. | |
| 2010/0113850 A1 * | 5/2010 | Ghosh | B01J 29/46 585/466 |
| 2013/0289325 A1 | 10/2013 | Yanagawa et al. | |
| 2016/0008796 A1 * | 1/2016 | Saka | B01J 29/005 502/68 |

FOREIGN PATENT DOCUMENTS

| | | | |
|---|---|---|---|
| CN | 104368377 A | | 2/2015 |
| CN | 106457231 A | | 2/2017 |
| EP | 0785178 B1 | | 3/1999 |
| WO | WO 2008/015027 | * | 2/2008 |
| WO | WO 2017/015597 | * | 1/2017 |

OTHER PUBLICATIONS

State Intellectual Property Office of China, International Search Report dated Aug. 8, 2020, in corresponding International Appln. No. PCT/CN2020/093983.

Chinese Patent Office, Office Action dated Jul. 2, 2021, in corresponding Chinese Patent Application No. 201910654576.2.

* cited by examiner

OLEFIN AROMATIZATION CATALYST, PREPARATION METHOD AND USE THEREOF, AND LOW-CARBON OLEFIN AROMATIZATION PROCESS

PRIORITY CLAIM & CROSS REFERENCE

This application claims priority to Chinese Application No. 201910654576.2, filed on Jul. 19, 2019, entitled "Aromatization Catalyst, and Preparation Method Thereof, and Low-Carbon Olefin Aromatization Process", which is specifically and entirely incorporated by reference.

FIELD

The present disclosure relates to the technical field of aromatizing low-carbon olefins into aromatic hydrocarbons, in particular to an aromatization catalyst, preparation method and use thereof and a low-carbon olefin aromatization process.

BACKGROUND

Since the ethane and ethylene are relatively inexpensive and their raw materials are readily available, more and more processes are shifted to the aromatization of alkanes or alkenes to produce light aromatic hydrocarbons (e.g., Benzene-Toluene-Xylene, or BTX). For example, US20090209794A1 discloses a process for the conversion of ethane to aromatic hydrocarbons, and the process comprises: (a) contacting ethane with a dehydroaromatization catalyst having 0.005-0.1 wt % platinum, an amount of gallium which is equal to or greater than the amount of platinum, from 10 to 99.9 wt % of aluminosilicate, and a binder; and (b) separating methane, hydrogen and $C_2$-$C_5$ hydrocarbons from the reaction products of step (a) to obtain aromatic reaction products including benzene. Firstly, the catalyst in the process must use noble metals (e.g., platinum), and the noble metals are combined with ZSM-5 molecular sieve to be used as the bi-functional catalyst; secondly, in order to activate ethane, the reaction temperature of the process is high and the reaction is carried out at 630° C., but the conversion rate of ethane is relatively low, e.g., not more than 70%; in addition, the catalyst is quickly deactivated, the activity of catalyst is lower than 40%, and the BTX yield is merely 30-40% in general even under the optimized conditions; thirdly, much of the ethane in the process is converted to low value methane, and the unconverted ethane and methane also lead to increasing difficulty in light hydrocarbon separation, recycling and recovering. Moreover, the high reaction temperature and the frequent regeneration treatment cause the noble metals to change from a nanoparticle state to a sintered state; in order to re-disperse the noble metals on the catalyst carrier, it is necessary to inject a chlorine-containing substance after decoking, the addition of halogen in a high-temperature and humid environment imposes higher requirements on the equipment and facility. Rapid deactivation of the catalyst also requires the use of more complex reactors, such as moving bed reactors, thereby increasing the operating cost.

EP0785178B1 discloses a process for producing aromatic hydrocarbon, and the process comprises: contacting a light hydrocarbon feedstock having olefins and/or paraffins with a zeolite catalyst in a fixed-bed, adiabatic reactor to thereby effect a catalytic cyclization reaction of the light hydrocarbon feedstock, wherein the catalytic cyclization reaction is performed under conditions which satisfy the following requirements: (1) the zeolite catalyst has an initial stage-catalytic activity of 0.2 ($sec^{-1}$) or more in terms of the initial stage, first-order reaction rate constant of the decomposition of n-hexane catalyzed by the zeolite catalyst; (2) the catalyst bed has a temperature of from 450° C. to 650° C.; (3) the catalyst bed exhibits a temperature distribution with respect to the distance from an inlet to an outlet of the catalyst bed, wherein the temperature distribution has at least one maximum temperature value; and (4) the temperature of the outlet of the catalyst bed is +/−40° C. relative to the temperature of the inlet of the catalyst bed. The process is suitable for aromatization of olefins with $C_4$ or above, and the selectivity of aromatic hydrocarbon is relatively low.

In addition, the prior art also comprises the aromatization reaction using olefin as raw material, The paper "Development of Process and Catalyst of Low-carbon Olefin Aromatization" (Li Yu, Zhang Ying-qiang, et al.) presents the property of ZSM-5 molecular sieve and its modified catalyst for the aromatization of low carbon olefins $C_2$-$C_5$, and the results show that the modified catalyst obtained by adding some metals such as Zn, Ga, Pt, Ni, Cd into the ZSM-5 molecular sieve can directly convert olefins and mixtures thereof into aromatic hydrocarbons, both the yield and selectivity of aromatic hydrocarbons are significantly improved. However, the improved yield and selectivity of catalyst is mainly derived from introducing metals, there still are problems that the coke content is high and the frequent regeneration treatment is required.

In summary, the prior art has the problems such as a large amount of methane is generated, coke is easily formed, the service life of the catalyst is short, the frequent regeneration treatment is required; in addition, the preparation of catalyst requires an use of one or more metal, even expensive noble metal.

SUMMARY

The present disclosure aims to overcome the problems in the prior art, such as easy deactivation and low stability of the catalyst causes the catalyst requires the frequent regeneration process, low conversion rate of reactant, one or more metal shall be used in a process of preparing the catalyst, thereby provides an aromatization catalyst, a preparation method and use thereof and a low-carbon olefin aromatization process. The aromatization catalyst can be used for carrying out aromatization reaction of low-carbon olefins to generate aromatic hydrocarbons, the catalyst has high stability, and the aromatic hydrocarbon products have desirable selectivity, the generation of methane and coke can be effectively reduced, and the metal may not be used in the aromatization catalyst.

In order to fulfill the above purposes, a first aspect of the present disclosure provides an olefin aromatization catalyst, wherein the aromatization catalyst comprises a microporous material, a binder and a modifier; the microporous material is a zeolite molecular sieve, the binder is alumina, the modifier is phosphorus, and the molar ratio of the aluminum element in the binder to the phosphorus element is more than or equal to 1 and less than 5; the ratio of the acidity of the strongly acidic sites to the acidity of the weakly acidic sites of the olefin aromatization catalyst is less than 1.

Preferably, the ratio of the acidity of the strongly acidic sites to the acidity of the weakly acidic sites is not more than 0.85, more preferably not more than 0.75.

Preferably, the microporous material is a zeolite molecular sieve having a MFI structure, preferably a ZSM-5 molecular sieve, and further preferably, the ZSM-5 molecular sieve has a silica-alumina ratio not more than 50.

Preferably, the weight ratio of the microporous material to the binder is 1:0.05-1, wherein the weight of said binder is calculated based on aluminum element therein.

Preferably, at least a portion of the binder and the modifier in the catalyst is present in a form of aluminum phosphate.

Preferably, the aromatization catalyst further comprises 0 wt %-1 wt % of metal active component based on the total amount of the aromatization catalyst, wherein the metal active component is one or more selected from the group consisting of Pt, Ni, Co, Cu, Zn, Fe, Pd, Rh, Ru, Re, Mo, W, Au and Ga.

A second aspect of the present disclosure provides a method for preparing an olefin aromatization catalyst, the process comprises the following steps:

mixing the microporous material, the alumina precursor and the phosphorus source, molding and calcining the mixture; or mixing the microporous material and an alumina precursor, molding and calcining the mixture, contacting it with a phosphorus source to load phosphorus element, subsequently carrying out a secondary calcination;

wherein the microporous material is a zeolite molecular sieve, the molar ratio of aluminum element in an alumina precursor to phosphorus element in a phosphorus source is more than 1 and less than 5, the temperatures of the calcination and secondary calcination are respectively within a range of 300° C.-700° C., preferably 450° C.-600° C.; the times are respectively within a range of 0.5-24 hours, preferably 2-8 hours.

Preferably, the weight ratio of the microporous material to the alumina precursor calculated in terms of aluminum element is 1:0.05-1.

Preferably, the microporous material is a zeolite molecular sieve having a MFI structure, more preferably a ZSM-5 molecular sieve, and further preferably, the ZSM-5 molecular sieve has a silica-alumina ratio not more than 50.

Preferably, the phosphorus source is a phosphorus-containing solution, and the loading mode is an impregnation method, such as a saturation impregnation method.

Preferably, the solute in the phosphorus-containing solution is one or more selected from the group consisting of phosphoric acid, ammonium phosphate, phosphine, and derivatives thereof.

Preferably, the phosphorus-containing solution has a content of phosphorus element within a range of 0.5 wt % to 30 wt %, more preferably 5 wt % to 15 wt %.

Preferably, the process further comprises subjecting the product obtained from the calcination process or the product obtained from the secondary calcination to a hydrothermal treatment, preferably, the conditions of the hydrothermal treatment comprise: the temperature is within a range of 250-650° C., and the time is within a range of 0.5-24 h.

Preferably, the process further comprises loading 0-1 wt % of metal active component on the product obtained from the calcination process or the product obtained from the secondary calcination, based on the total amount of the catalyst.

Preferably, the metal active component is one or more selected from the group consisting of Pt, Ni, Co, Cu, Zn, Fe, Pd, Rh, Ru, Re, Mo, W, Au and Ga.

A third aspect of the present disclosure provides a low-carbon olefin aromatization process, the process comprises the following steps: contacting low-carbon olefin with hydrogen in the presence of a catalyst under the aromatization conditions, wherein the catalyst is the aforementioned olefin aromatization catalyst;

preferably, the low-carbon olefin is $C_2$-$C_6$ olefin, preferably ethylene;

preferably, the aromatization conditions comprise: the pressure is 0.01 MPa-2 MPa in terms of the gauge pressure; the temperature is within a range of 300° C.-700° C., preferably 500° C.-650° C.; the volume ratio of hydrogen to the olefin is 0.1-5, preferably 0.5-2; the volume hourly space velocity (VHSV) of the low-carbon olefin is 500 $h^{-1}$ to 50,000 $h^{-1}$, and preferably 1,000 $h^{-1}$ to 10,000 $h^{-1}$.

The present disclosure also provides an application of the olefin aromatization catalyst and the preparation process thereof in the aromatization of low-carbon olefins.

Preferably, the aromatization catalyst comprises a zeolite molecular sieve, a binder, and a modifier, and optionally a metal active component; the binder is a compound containing an aluminum element and a phosphorus element, and the molar ratio of the aluminum element to the phosphorus element is more than or equal to 1 and less than 5; the ratio of the acidity of the strongly acidic sites to the acidity of the weakly acidic sites of the aromatization catalyst is less than 1.

Preferably, the binder is aluminum phosphate and optionally alumina.

Preferably, the preparation process of the aforementioned aromatization catalyst comprises the following steps:

(a) mixing the microporous material, alumina and a phosphorus-containing solution, extruding and calcining the extrudate to obtain a molded product, wherein the molar ratio of aluminum element in the alumina to phosphorus element in the phosphorus-containing solution is more than 1 and less than 5;

(b1) optionally, subjecting the molded product to a hydrothermal treatment; and/or (b2) optionally, loading the metal active component on the surface of the molded product.

Preferably, the preparation method of the aforementioned aromatization catalyst comprises the following steps:

(A) mixing the microporous material and the alumina and extruding the mixture, and optionally carrying out a hydrothermal treatment, to obtain an extrudate;

(B) mixing the extrudate and a phosphorus-containing solution, extruding and calcining the extrudate to obtain a catalyst, wherein the molar ratio of aluminum element in alumina to phosphorus element in the phosphorus-containing solution is more than 1 and less than 5;

(C) optionally, loading a metal active component on the catalyst surface.

The ratio of the acidity of the strong acid sites to the acidity of the weak acid sites of the aromatization catalyst is less than 1, preferably less than 0.75; the binder in the aromatization catalyst comprises aluminum element and phosphorus element, and the molar ratio of the aluminum element to the phosphorus element is more than 1 and less than 5. The aromatization catalyst in the present disclosure can be used for the aromatization reaction of the low-carbon olefins in a wider temperature range to produce aromatic hydrocarbons, and obtain the aromatic hydrocarbons with high yield with the minimum generation amount of coke and methane, and prolong the service life of the catalyst. Moreover, the raw materials of the present disclosure may be directly derived from an ethane cracker without the purification and separation operations, thereby further reducing the production cost.

In addition, the catalyst of the present disclosure may be prepared without using a metal, it not only reduces the production cost of the catalyst, but also saves the equipment cost increased by the catalyst regeneration process containing halogen.

DETAILED DESCRIPTION

Figure 1:
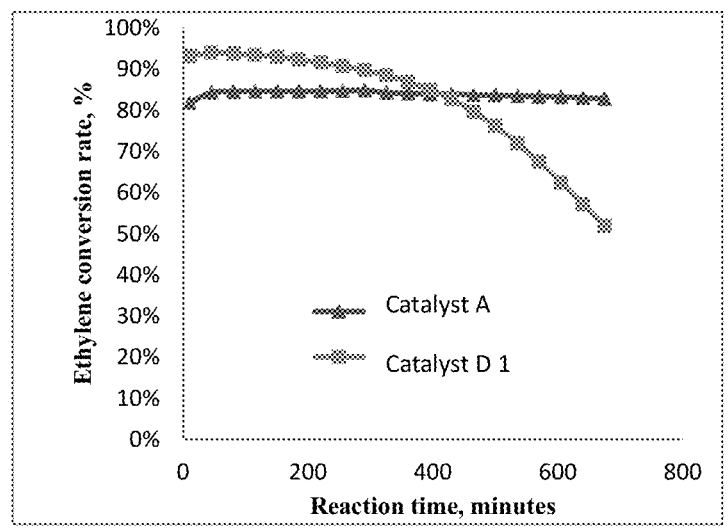
FIG. 1 illustrates a graph comparing the ethylene conversion rates of catalyst A of the present disclosure and catalyst D1 of the Comparative Example.

The terminals and any value of the ranges disclosed herein are not limited to the precise ranges or values, such ranges or values shall be comprehended as comprising the values adjacent to the ranges or values. As for numerical ranges, the endpoint values of the various ranges, the endpoint values and the individual point value of the various ranges, and the individual point values may be combined with one another to produce one or more new numerical ranges, which should be deemed have been specifically disclosed herein.

The present disclosure provides an olefin aromatization catalyst, which comprises zeolite molecular sieve microporous material, alumina binder, phosphorus modifier, and an optional metal active component; the molar ratio of aluminum element to phosphorus element in the binder is more than or equal to 1 and less than 5; the ratio of the acidity of the strongly acidic sites to the acidity of the weakly acidic sites of the aromatization catalyst is less than 1.

In the present disclosure, the weakly acidic site means the $NH_3$-TPD peak having a maximum desorption temperature less than 300° C., such as 180° C.-230° C.; the strongly acidic site refers to the $NH_3$-TPD peak having a maximum desorption temperature not less than 300° C., for example, within a range of 300° C.-400° C. In particular, the test method is the customary method in the art, namely a method of characterizing the acid site with temperature-programmed desorption (TPD). The amount of ammonia desorbed at different temperatures can be detected by a thermal conductivity detector (TCD) disposed in the $NH_3$-TPD instrument to obtain the acidity of different sites.

In the present disclosure, the method and steps for characterizing acid sites of the catalyst can be as follows: weighing 0.2 g catalyst, filling the catalyst into a quartz sample tube, raising the temperature to 450° C. in a programed manner under the condition with presence of helium gas, activating for 1 h, then cooling to 150° C., adsorbing ammonia gas for 30 min, subsequently switching to purging with helium gas, removing excessive ammonia gas until the baseline of the detector is stable, raising the temperature to 600° C. with a programmed manner at the temperature rise rate of 10° C./min, and detecting the ammonia desorption amount of the sample by a thermal conductivity detector (TCD) disposed in the $NH_3$-TPD instrument, the ratio of the desorption amounts is exactly the acidity ratio.

In the present disclosure, the ratio of the acidity of the strongly acidic sites to the acidity of the weakly acidic sites of the aromatization catalyst is less than 1, that is, the acidity of the strongly acidic sites is less than the acidity of the weakly acidic sites, preferably, the ratio of the acidity of the strongly acidic sites to the acidity of the weakly acidic sites is not more than 0.85, and further preferably not more than 0.75.

In the present disclosure, the microporous material is preferably a zeolite molecular sieve having a MFI structure, preferably a ZSM-5 molecular sieve, and further preferably, the silica-alumina ratio of the ZSM-5 molecular sieve is not more than 50, for example, the silica-alumina ratio of the ZSM-5 molecular sieve is 10, 15, 20, 25, 30, 35, 40, 45, 50, and a random value within the range of any two of the numerical values. The silicon-aluminum ratio in the present disclosure refers to the molar ratio of $SiO_2/Al_2O_3$.

It is predictable that a portion of the binder alumina and the modifier phosphorus in the present disclosure form aluminum phosphate species, and thus the binder contains aluminum phosphate and optionally alumina. That is, the binder is aluminum phosphate, or a mixture of aluminum phosphate and alumina.

In the present disclosure, preferably, the metal active component is one or more selected from the group consisting of Pt, Ni, Co, Cu, Zn, Fe, Pd, Rh, Ru, Re, Mo, W, Au and Ga.

In the present disclosure, preferably, the weight ratio of the microporous material to the binder is 1:0.05-1, wherein the binder is calculated in terms of aluminum element in the binder. For example, the weight ratio of the microporous material to the binder is 1:0.05, 1:0.1, 1:0.15, 1:0.2, 1:0.25, 1:0.3, 1:0.35, 1:0.4, 1:0.45, 1:0.5, 1:0.55, 1:0.6, 1:0.65, 1:0.7, 1:0.75, 1:0.8, 1:0.85, 1:0.9, 1:0.95, 1:1, and a random value within the range of any two of the numerical values.

In the present disclosure, the content of the metal active component is preferably 0 wt % to 1 wt %, preferably 0 wt % to 0.5 wt %, based on the total amount of the aromatization catalyst. For example, the content of the metal active component is 0 wt %, 0.001 wt %, 0.01 wt %, 0.05 wt %, 0.1 wt %, 0.5 wt %, and a random value within the range of any two of the numerical values, based on the total amount of the aromatization catalyst. In the present disclosure, the aromatization catalyst may not contain a metal active component, it not only reduces the production cost of the catalyst, but also saves the equipment cost increased by the catalyst regeneration process containing halogen.

In the present disclosure, the contents of the microporous material, the binder and the metal active component may be measured by an Inductively Coupled Plasma (ICP) or an X-Ray Fluorescence (XRF), or may be calculated based on the feeding amounts. The contents in the Examples of the present disclosure are measured with an Energy Dispersive X-ray Detector EDX-7000 from Shimadzu Corporation in Japan.

A second aspect of the present disclosure provides a preparation method of the aforementioned olefin aromatization catalyst, the method comprises the steps of mixing, molding, calcining and the like. The microporous material, the binder precursor and the modifier precursor phosphorus source can be mixed together, molded and calcined, or the microporous material and the binder precursor may be initially mixed and molded, then the modifier precursor phosphorus source is loaded. In order to convert the binder precursor and the modifier precursor into the binder and modifier required for the catalyst, a calcination step is required. The method of loading the phosphorus source may be an impregnation method, such as the saturation impregnation method or the equivalent-volume impregnation method.

In the present disclosure, the corresponding substance which needs to be calcined to obtain the required components of the catalyst is called as a precursor. For example, a precursor of the binder alumina may be aluminum hydroxide in various forms, or a hydrate thereof such as pseudo-boehmite, the precursor of the modifier phosphorus may be various substances, such as phosphoric acid, ammonium phosphate, which are decomposed to phosphorus element after the calcination process, and the precursor of the phosphorus is also called a phosphorus source. Similarly, the precursor of the metal active component may be a soluble salt of the respective metal component, such as one or more selected from the group consisting of chloride, nitrate, sulphate and phosphate.

When the catalyst further comprises a metal active component, the metal active component can be obtained through an impregnation step. The metal active component may be loaded along with phosphorus or sequentially with phosphorus, for example, phosphorus is initially loaded and the metal active component is then loaded.

In the present disclosure, the calcination process may be carried out after all the necessary components are loaded, or may be implemented for several times after each of the components is loaded, the calcination process may be performed for once or multiple times. The conditions for each calcination process may be the same or different.

According to a specific embodiment of the present disclosure, the method of the present disclosure may further comprise a hydrothermal treatment step. The hydrothermal treatment step is performed after the calcination process. The hydrothermal treatment step may be carried out after one or more calcination process, or may be implemented after the last time of calcination process.

According to an embodiment of the present disclosure, the preparation method of the catalyst comprises the following steps:

(a) mixing the microporous material, alumina and a phosphorus-containing solution, extruding and calcining the extrudate to obtain a catalyst, wherein the molar ratio of aluminum element in the alumina to phosphorus element in the phosphorus-containing solution is more than 1 and less than 5;

(b1) optionally, subjecting the catalyst to a hydrothermal treatment; and/or (b2) optionally, loading a metal active component on the catalyst surface.

According to another embodiment of the present disclosure, the preparation method of the aforementioned catalyst comprises the following steps:

(A) mixing the microporous material and the alumina and extruding the mixture, and optionally carrying out a hydrothermal treatment, to obtain an extrudate;

(B) mixing the extrudate and a phosphorus-containing solution, extruding and calcining the extrudate to obtain a catalyst, wherein the molar ratio of aluminum element in alumina to phosphorus element in the phosphorus-containing solution is more than 1 and less than 5;

(C) optionally, loading a metal active component on the catalyst surface.

Specifically, the following embodiments may be adopted:

(I) initially mixing the microporous material, the binder precursor and the modifier precursor phosphorus source (e.g., phosphorus-containing solution), extruding and calcining the extrudate to prepare the desirable catalyst; or (II) initially mixing the microporous material, the binder precursor and the modifier precursor phosphorus source (e.g., phosphorus-containing solution), extruding and calcining the extrudate, and then subjecting the calcined product to a hydrothermal treatment (calcination+hydrothermal treatment) to prepare the desirable catalyst; or (III) initially mixing the microporous material, the binder precursor and the modifier precursor phosphorus source (e.g., phosphorus-containing solution), extruding and calcining the extrudate, then subjecting the calcined product to a hydrothermal treatment, impregnating a product obtained from the hydrothermal treatment with a solution containing a metal active component, and subsequently calcination again (calcination+hydrothermal treatment+loading+calcination) to prepare the desirable catalyst; or (IV) initially mixing the microporous material, the binder precursor and the modifier precursor phosphorus source (e.g., phosphorus-containing solution), extruding and calcining the extrudate, then impregnating the calcined product with a solution containing a metal active component, calcining again, subsequently subjecting the product obtained from the re-calcining process to a hydrothermal treatment (calcining+loading+calcining+hydrothermal treatment) to prepare the desirable catalyst; or (V) initially mixing the microporous material, the binder precursor and the modifier precursor phosphorus source (e.g., phosphorus-containing solution), extruding and calcining the extrudate, then subjecting the calcined product to a hydrothermal treatment, impregnating a product obtained from the hydrothermal treatment with a solution containing a metal active component, and subsequently calcination again, subjecting the product obtained from the re-calcination process to a further hydrothermal treatment (calcination+hydrothermal treatment+impregnation+calcination+hydrothermal treatment) to prepare the desirable catalyst; or (VI) mixing the microporous material and the binder precursor uniformly, extruding and molding the mixture, then calcining, loading the modifier phosphorus on the calcined product, subsequently calcining for the second time to prepare the desirable catalyst; or (VII) mixing the microporous material and the binder precursor uniformly, extruding and molding the mixture, then calcining, subjecting the calcined product to a hydrothermal treatment, loading modifier phosphorus on the product obtained after the hydrothermal treatment, subsequently carrying out the secondary calcining (calcining+hydrothermal treatment+loading+calcining) to prepare the desirable catalyst; or (VIII) mixing the microporous material and the binder precursor uniformly, extruding and molding the mixture, then calcining, subjecting the calcined product to a hydrothermal treatment, simultaneously or sequentially loading the modifier phosphorus and the metal active component on the product obtained after the hydrothermal treatment, subsequently carrying out the secondary calcining (calcining+hydrothermal treatment+loading+calcining) to prepare the desirable catalyst; or (IX) mixing the microporous material and the binder precursor uniformly, extruding and molding the mixture, then calcining, loading the modifier phosphorus on the calcined product, subsequently carrying out the second calcination, further loading the calcined produce with a metal active component, and carrying out the third calcination (calcining+loading+calcining+loading+calcining), thereby prepare the desirable catalyst; or (X) mixing the microporous material and the binder precursor uniformly, extruding and molding the mixture, then calcining, subjecting the calcined product to a hydrothermal treatment, loading the modifier phosphorus on the product obtained after the hydrothermal treatment, carrying out the secondary calcination, further loading a metal active component on the calcined product, and subsequently carrying out the third calcination (calcining+hydrothermal treatment+loading+calcining+loading+calcining), thereby prepare the desirable catalyst; or (XI) mixing the microporous material and the binder precursor uniformly, extruding and molding the mixture, then calcining, loading a modifier phosphorus on the calcined product, carrying out the secondary calcination, subsequently loading a metal active component on the calcined product, carrying out the third calcination, further subjecting the calcined product to a hydrothermal treatment (calcining+loading+calcining+loading+calcining+hydrothermal treatment) to prepare the desirable catalyst;

(XII) mixing the microporous material and the binder precursor uniformly, extruding and molding the mixture, then calcining, subjecting the calcined product to a hydrothermal treatment, loading the modifier phosphorus on the product obtained after the hydrothermal treatment, carrying out the secondary calcination, further loading a metal active component on the calcined product, and subsequently carrying out the third calcination, further carrying out secondary hydrothermal treatment (calcining+hydrothermal treatment+loading+calcining+loading+calcining+hydrothermal treatment), thereby prepare the desirable catalyst.

The catalysts obtained from the modes (I) to (V) have higher activity and aromatic hydrocarbon selectivity, and are more suitable for raw materials having a low content of olefins; the catalysts obtained from the modes (VI) to (XII) exhibit favorable carbon deposition resistance, and are more suitable for being applied in a fixed bed reactor.

According to the method of the present disclosure, preferably, the weight ratio of the microporous material to the alumina calculated based on the aluminum element is 1:0.05 to 1. For example, the weight ratio of the microporous material to alumina calculated based on the aluminum element is 1:0.05, 1:0.1, 1:0.15, 1:0.2, 1:0.25, 1:0.3, 1:0.35, 1:0.4, 1:0.45, 1:0.5, 1:0.55, 1:0.6, 1:0.65, 1:0.7, 1:0.75, 1:0.8, 1:0.85, 1:0.9, 1:0.95, 1:1, and a random value within the range of any two of the numerical values. In a preferred embodiment of the present disclosure, by adding a specific amount of a phosphorus-containing solution while limiting the microporous material and alumina, and the concentration of the phosphorus-containing solution, the acidity of the strongly acidic sites of the aromatization catalyst prepared by the present disclosure is smaller than that of the weakly acidic sites, an use of the aromatization catalyst not only can generate the aromatic hydrocarbons with high selectivity, but also produce coke in a smaller amount, further improve the regeneration performance and prolong the service life of catalyst.

According to the method of the present disclosure, the precursor of phosphorus is preferably a phosphorus-containing solution, such that the loading of phosphorus can be performed with an impregnation method, or the mixing of the microporous material and the binder precursor can be directly implemented. The solvent in the phosphorus-containing solution may be water. Preferably, the solute in the phosphorus-containing solution is one or more selected from the group consisting of phosphoric acid, ammonium phosphate, phosphine, and derivatives thereof.

According to the method of the present disclosure, preferably, the content of the phosphorus element in the phosphorus-containing solution is 0.5 wt % to 30 wt %, preferably 5 wt % to 15 wt %. For example, 5 wt %, 6 wt %, 7 wt %, 8 wt %, 9 wt %, 10 wt %, 11 wt %, 12 wt %, 13 wt %, 14 wt %, 15 wt %, and a random value within the range of any two of the numerical values. When the phosphorus content is within the preferred range, the prepared aromatization catalyst has favorable performance.

According to the method of the present disclosure, preferably, the microporous material may be a variety of molecular sieve having an MFI structure, preferably a ZSM-5 molecular sieve, and further particularly preferably, the silica-alumina molar ratio of ZSM-5 molecular sieve is not more than 50. In a preferred circumstance, the present disclosure limits the mole ratio of silicon to aluminum to be not more than 50, such that the catalyst prepared by the present disclosure has higher ethylene conversion rate and aromatic selectivity and less amount of generated coke.

According to the method of the present disclosure, the mode of the hydrothermal treatment is to contact the material to be treated with water vapor, and preferably, the conditions of the hydrothermal treatment comprise: the temperature is 250-650° C., and the time is 0.5-24 h. The conditions for each hydrothermal treatment process may be the same or different within the aforementioned mentioned ranges.

According to the method of the present disclosure, the metal active component is one or more selected from the group consisting of Pt, Ni, Co, Cu, Zn, Fe, Pd, Rh, Ru, Re, Mo, W, Au and Ga. The loading method may be a conventional method in the art, such as an impregnation method. The manner of introducing the above-mentioned metal active component can be obtained by adding a compound containing the metal active component, compound containing the metal active component is preferably one or more selected from the group consisting of chlorides, nitrates, sulfates, acetates and oxalates of the active metal element. For example, the mode of introducing Pt may be adding a $Pt(NO_3)_2$ solution.

According to the method of the present disclosure, preferably, the calcination conditions include: the temperature is 300-700° C., preferably 450-600° C.; the time is 0.5 to 24 hours, preferably 2 to 8 hours. The conditions for each calcination process may be the same or different within the aforementioned ranges.

The present disclosure also provides a low-carbon olefin aromatization process by using the aforementioned catalyst, the process comprises the following steps: contacting the low-carbon olefin, hydrogen and the olefin aromatization catalyst under the aromatization conditions.

According to the process of the present disclosure, the low-carbon olefin may contain hydrogen and other hydrocarbons (e.g., unconverted ethane) and the like, as a result, the raw materials of the low-carbon olefins of the present disclosure may be directly derived from an ethane cracker without the purification and separation operations.

According to the process, the low-carbon olefins may be $C_2$-$C_6$ olefins, for example, the low-carbon olefin may be one or more selected from the group consisting of ethylene, propylene, 1-butene, 2-butene, n-pentene, 2-pentene, 1-hexene, 2-hexene, 3-hexene and 2-methyl-1-pentene. Further preferably, the content of total hydrocarbons in the low-carbon olefins is not less than 60 vol %, wherein the content of ethylene is not less than 30 vol %; further preferably, the low-carbon olefin is ethylene.

According to the process of the present disclosure, the conditions of the low-carbon hydrocarbon aromatization reaction may preferably comprise: the pressure is 0.01 MPa-2 MPa in terms of the gauge pressure; the temperature is within a range of 300° C.-700° C., preferably 500° C.-650° C.; the volume ratio of hydrogen to the olefin is 0.1-5, preferably 0.5-2; the volume hourly space velocity (VHSV) of the olefin is 500 h$^{-1}$ to 50,000 h$^{-1}$, and preferably 1,000 h$^{-1}$ to 10,000 h$^{-1}$.

According to the process of the present disclosure, preferably, the method further comprises a preheating step before contacting the low-carbon olefin, hydrogen and the catalyst. The preheating operation may be as follows: at atmospheric pressure, H$_2$ is introduced into the reactor at a flow rate of 66.7 sccm and the reactor is heated to 630° C. at a temperature rise rate of 15° C./min, and then maintain the temperature for 30 min.

According to the process of the present disclosure, preferably, when the low-carbon olefin and the hydrogen are introduced, N$_2$ is also introduced, wherein N$_2$ is used as an internal standard substance for chromatographic analysis.

According to the process of the present disclosure, a fixed bed reactor is preferably used in the low-carbon hydrocarbon aromatization reaction.

The present disclosure will be described in detail below with reference to the examples.

In the following Examples and Comparative Examples, the ZSM-5 molecular sieve having a silicon-aluminum ratio of 30 is purchased from Sigma-Aldrich Inc.;

the alumina precursor may be aluminum hydroxide which is purchased from Sasol Company and has a product name Catapal B or is purchased from Sigma-Aldrich Inc., and the weight is calculated in terms of alumina;

the gas chromatography is purchased from Agilent Corporation Ltd., and the model number is 7890;

the conversion rate of ethylene is calculated according to Formula 1:

conversion rate of ethylene %=(total mole number of ethylene−remaining mole number of ethylene)/ total mole number of ethylene×100%  (Formula 1)

The selectivity of a substance X is calculated according to Formula 2:

selectivity of substance $X$ %=total mole number of substance $X$ in the product/mole number of converted ethylene carbon×100%  (Formula 2)

The yield of substance X is calculated according to Formula 3:

Yield of substance $X$ %=conversion rate of ethylene %×selectivity of substance $X$ %  (Formula 3)

In the following Examples, the contents of the microporous material, the binder and the metal active component are measured with an Energy Dispersive X-ray Detector EDX-7000 from Shimadzu Corporation in Japan.

Example 1

7 g ZSM-5 molecular sieve (having a silica-alumina ratio of 30), 1.77 g SASOL alumina precursor and 2 g phosphoric acid aqueous solution (the phosphoric acid concentration is 85 wt %) were mixed and extruded to obtain an extrudate, the extrudate was calcined at a temperature of 550° C. for 2 hours, and the calcined product was pulverized and sieved to obtain 30-mesh particles, the prepared aromatization catalyst was labeled as catalyst A.

Wherein the aromatization catalyst comprises a microporous material and a binder, the molar ratio of aluminum element to phosphorus element in the binder is 2; the weight ratio of the microporous material to the binder is 1:0.13, wherein the weight of said binder is calculated in terms of the aluminum element therein.

Example 2

7 g ZSM-5 molecular sieve (having a silica-alumina ratio of 30), 1.25 g alumina precursor from the Sigma-Aldrich Inc. and 2.84 g phosphoric acid aqueous solution (the phosphoric acid concentration is 85 weight percent) were mixed and extruded to obtain an extrudate, the extrudate was calcined at a temperature of 550° C. for 2 hours, and the calcined product was pulverized and sieved to obtain 20-mesh particles, the prepared aromatization catalyst was labeled as catalyst B.

Wherein the aromatization catalyst comprises a microporous material and a binder, the molar ratio of aluminum element to phosphorus element in the binder is 1; the weight ratio of the microporous material to the binder is 1:0.09, wherein the weight of said binder is calculated in terms of the aluminum element therein.

Example 3

7 g ZSM-5 molecular sieve (having a silica-alumina ratio of 30), 2 g SASOL alumina precursor and 18.5 g ammonium phosphate aqueous solution (the content of ammonium phosphate is 10 wt %) were mixed and extruded to obtain an extrudate, the extrudate was calcined at a temperature of 550° C. for 2 hours, and the calcined product was pulverized and sieved to obtain 40-mesh particles, the prepared aromatization catalyst was labeled as catalyst C.

Wherein the aromatization catalyst comprises a microporous material and a binder, the molar ratio of aluminum element to phosphorus element in the binder is 3:2; the weight ratio of the microporous material to the binder is 1:0.15, wherein the weight of said binder is calculated in terms of the aluminum element therein.

Example 4

7 g ZSM-5 molecular sieve (having a silica-alumina ratio of 30), 1.77 g SASOL alumina precursor and 2 g phosphoric acid aqueous solution (the phosphoric acid concentration is 85 wt %) were mixed and extruded to obtain an extrudate, the extrudate was calcined at a temperature of 550° C. for 2 hours, and the calcined product was pulverized and sieved to obtain 30-mesh particles, the particles were further subjected to a hydrothermal treatment with an air containing 20% by weight of water vapor and a flow rate of 150 mL/min at a temperature of 600° C. for 4 hours, the prepared aromatization catalyst was labeled as catalyst D.

Wherein the aromatization catalyst comprises a microporous material and a binder, the molar ratio of aluminum element to phosphorus element in the binder is 2; the weight ratio of the microporous material to the binder is 1:0.13, wherein the weight of said binder is calculated in terms of the aluminum element therein.

Example 5

7 g ZSM-5 molecular sieve (having a silica-alumina ratio of 30) and 1.77 g SASOL alumina precursor were mixed and extruded to obtain an extrudate, the extrudate was calcined at a temperature of 550° C. for 2 hours, and the calcined product was pulverized and sieved to obtain 30-mesh particles, the particles were then impregnated with 2 g aqueous phosphoric acid solution (the phosphoric acid concentration is 85 wt %), and the impregnated articles were calcined at a temperature of 550° C. for 2 hours, the prepared aromatization catalyst was labeled as catalyst E.

Wherein the aromatization catalyst comprises a microporous material and a binder, the molar ratio of aluminum element to phosphorus element in the binder is 2; the weight ratio of the microporous material to the binder is 1:0.13, wherein the weight of said binder is calculated in terms of the aluminum element therein.

Example 6

7 g ZSM-5 molecular sieve (having a silica-alumina ratio of 30) and 1.77 g SASOL alumina precursor were mixed and extruded to obtain an extrudate to obtain an extrudate, the extrudate was calcined at a temperature of 550° C. for 2 hours, and the calcined product was pulverized and sieved to obtain 30-mesh particles, the particles were then impregnated with 2 g aqueous phosphoric acid solution (the phosphoric acid concentration is 85 wt %), and the impregnated articles were calcined at a temperature of 550° C. for 2 hours, the particles were further subjected to a hydrothermal treatment with an air containing 20% by weight of water vapor and a flow rate of 150 mL/min at a temperature of 600° C. for 4 hours, the prepared aromatization catalyst was labeled as catalyst F.

Wherein the aromatization catalyst comprises a microporous material and a binder, the molar ratio of aluminum element to phosphorus element in the binder is 2; the weight ratio of the microporous material to the binder is 1:0.13, wherein the weight of said binder is calculated in terms of the aluminum element therein.

Example 7

7 g ZSM-5 molecular sieve (having a silica-alumina ratio of 30), 1.77 g SASOL alumina precursor and 2 g phosphoric acid aqueous solution (the phosphoric acid concentration is 85 wt %) were mixed and extruded to obtain an extrudate, the extrudate was calcined at a temperature of 550° C. for 2 hours, and the calcined product was pulverized and sieved to obtain 30-mesh particles;

5 g particles were then impregnated with an aqueous solution of Pt(NO$_3$)$_2$ having a concentration of 0.25 wt % at 25° C. for 2 hours to obtain a mixture, the obtained mixture was heated to 80° C. in a rotary evaporator and subjected to rotary evaporation for 60 minutes to obtain a dried product, and the product was subsequently calcined at a temperature of 550° C. for 2 hours to prepare an aromatization catalyst having a Pt content of 500 ppm, the prepared aromatization catalyst was labeled as catalyst G.

Wherein the aromatization catalyst comprises a microporous material, a binder and a metal active component, the molar ratio of aluminum element to phosphorus element in the binder is 2; the weight ratio of the microporous material to the binder is 1:0.13, wherein the weight of said binder is calculated in terms of the aluminum element therein; the content of the metal active component was 0.05 wt % based on the total amount of the aromatization catalyst.

Example 8

7 g ZSM-5 molecular sieve (having a silica-alumina ratio of 30), 1.77 g SASOL alumina precursor and 2 g phosphoric acid aqueous solution (the phosphoric acid concentration is 85 wt %) were mixed and extruded to obtain an extrudate, the extrudate was calcined at a temperature of 550° C. for 2 hours, and the calcined product was pulverized and sieved to obtain 30-mesh particles; the particles were further subjected to a hydrothermal treatment with an air containing 20% by weight of water vapor and a flow rate of 150 mL/min at a temperature of 600° C. for 4 hours to obtain a product, 5 g product was then impregnated with an aqueous solution of Pt(NO$_3$)$_2$ having a concentration of 0.25 wt % at 25° C. for 2 hours, the obtained mixture was heated to 80° C. in a rotary evaporator and subjected to rotary evaporation for 60 minutes to obtain a dried product, and the product was subsequently calcined at a temperature of 550° C. for 2 hours to prepare an aromatization catalyst having a Pt content of 500 ppm, the prepared aromatization catalyst was labeled as catalyst H.

Wherein the aromatization catalyst comprises a microporous material, a binder and a metal active component, the molar ratio of aluminum element to phosphorus element in the binder is 2; the weight ratio of the microporous material to the binder is 1:0.13, wherein the weight of said binder is calculated in terms of the aluminum element therein; the content of the metal active component was 0.05 wt % based on the total amount of the aromatization catalyst.

Example 9

7 g ZSM-5 molecular sieve (having a silica-alumina ratio of 30) and 1.77 g SASOL alumina precursor were mixed and extruded to obtain an extrudate, the extrudate was calcined at a temperature of 550° C. for 2 hours, and the calcined product was pulverized and sieved to obtain 30-mesh particles; the particles were then impregnated with 2 g aqueous phosphoric acid solution (the phosphoric acid concentration is 85 wt %), and the impregnated articles were calcined at a temperature of 550° C. for 2 hours, the particles were further subjected to a hydrothermal treatment with an air containing 20% by weight of water vapor and a flow rate of 150 mL/min at a temperature of 600° C. for 4 hours to obtain a product, 5 g product was then impregnated with an aqueous solution of Pt(NO$_3$)$_2$ having a concentration of 0.25 wt % at 25° C. for 2 hours, the obtained mixture was heated to 80° C. in a rotary evaporator and subjected to rotary evaporation for 60 minutes to obtain a dried product, and the product was subsequently calcined at a temperature of 550° C. for 2 hours to prepare an aromatization catalyst having a Pt content of 500 ppm, the prepared aromatization catalyst was labeled as catalyst I.

Wherein the aromatization catalyst comprises a microporous material, a binder and a metal active component, the molar ratio of aluminum element to phosphorus element in the binder is 2; the weight ratio of the microporous material to the binder is 1:0.13, wherein the weight of said binder is calculated in terms of the aluminum element therein; the content of the metal active component was 0.05 wt % based on the total amount of the aromatization catalyst.

Comparative Example 1

7 g ZSM-5 (having a silica-alumina ratio of 30) and 3 g SASOL alumina precursor were mixed and extruded to obtain an extrudate, the extrudate was calcined at a temperature of 550° C. for 2 hours, the calcined product was pulverized and sieved to obtain 30-mesh particles, the prepared aromatization catalyst was labeled as catalyst D1.

Comparative Example 2

7 g ZSM-5 molecular sieve (having a silica-alumina ratio of 30), 2.8 g SASOL alumina precursor and 0.32 g phosphoric acid aqueous solution (the phosphoric acid concentration is 85 wt %) were mixed and extruded, the extrudate was calcined at a temperature of 550° C. for 2 hours, and the calcined product was pulverized and sieved to obtain 30-mesh particles, the prepared aromatization catalyst was labeled as catalyst D2. Wherein the aromatization catalyst comprises a microporous material and a binder, the molar ratio of aluminum element to phosphorus element in the binder is 20.

Comparative Example 3

7 g ZSM-5 molecular sieve (having a silica-alumina ratio of 30), 2.0 g SASOL alumina precursor and 5 g phosphoric acid aqueous solution (the phosphoric acid concentration is 85 wt %) were mixed and extruded, the extrudate was calcined at a temperature of 550° C. for 2 hours, and the calcined product was pulverized and sieved to obtain 30-mesh particles, the prepared aromatization catalyst was labeled as catalyst D3. Wherein the aromatization catalyst comprises a microporous material and a binder, the molar ratio of aluminum element to phosphorus element in the binder is 0.9.

Test Example

Acid Site Characterization 0.2 g of catalysts A-I and catalysts D1-D5 were respectively weighted, and filled into a quartz sample tube, the temperature was raised to 450° C. in a programmed manner under the condition with presence of helium gas, the catalysts were activated for 1 h and then cooled to 150° C., and subjected to adsorption of ammonia gas for 30 min, subsequently switching to purging with helium gas, removing excessive ammonia gas until the baseline of the detector was stable, raising the temperature to 600° C. with a programmed manner at the temperature rise rate of 10° C./min, and the ammonia desorption amount of the samples was detected by a thermal conductivity detector (TCD) disposed in the $NH_3$-TPD instrument (with a model number AutoChem 2920 produced by the Micromeritics Instrument Corporation). The characterization results were shown in Table 1.

TABLE 1

| Catalysts | The acidity of the weakly acidic sites of the catalyst, mmol/g | The peak temperature of weakly acidic sites, °C. | The acidity of the strongly acidic sites, mmol/g | The peak temperature of strongly acidic sites, °C. | The ratio of the acidity of the strongly acidic sites to the acidity of the weakly acidic sites of the olefin aromatization catalyst |
|---|---|---|---|---|---|
| A | 0.09 | 218 | 0.065 | 324 | 0.72 |
| B | 0.072 | 215 | 0.041 | 305 | 0.57 |
| C | 0.152 | 224 | 0.132 | 365 | 0.87 |
| D | 0.09 | 218 | 0.055 | 323 | 0.61 |
| E | 0.075 | 216 | 0.045 | 308 | 0.6 |
| F | 0.070 | 215 | 0.044 | 307 | 0.63 |
| G | 0.09 | 218 | 0.065 | 324 | 0.72 |
| H | 0.09 | 218 | 0.055 | 323 | 0.61 |
| I | 0.070 | 215 | 0.044 | 307 | 0.63 |
| RA | 0.09 | 220 | 0.064 | 322 | 0.71 |
| D1 | 0.22 | 228 | 0.286 | 396 | 1.3 |
| D2 | 0.215 | 225 | 0.258 | 385 | 1.2 |
| D3 | 0.025 | 196 | 0.032 | 304 | 1.21 |
| D4 | 0.107 | 220 | 0.125 | 352 | 1.17 |
| D5 | 0.012 | 197 | 0.013 | 295 | 1.08 |

Comparative Example 4

7 g ZSM-5 (having a silica-alumina ratio of 30) and 3 g SASOL alumina precursor were mixed and extruded to obtain an extrudate, the extrudate was calcined at a temperature of 550° C. for 2 hours, the calcined product was pulverized and sieved to obtain 30-mesh particles, the particles were subjected to a hydrothermal treatment at a temperature of 600° C. for 4 hours, the prepared aromatization catalyst was labeled as catalyst D4.

Comparative Example 5

7 g ZSM-5 molecular sieve (having a silica-alumina ratio of 30) and 0.81 g phosphoric acid aqueous solution (the phosphoric acid concentration is 85 wt %) were mixed and dried, then mixed with 2.5 g SASOL alumina precursor and the mixture was extruded to obtain an extrudate, the extrudate was calcined at a temperature of 550° C. for 2 hours, and the calcined product was pulverized and sieved to obtain 30-mesh particles, the prepared aromatization catalyst was labeled as catalyst D5. Wherein the catalyst comprises a microporous material and a binder, the molar ratio of aluminum element to phosphorus element in the binder is 7.

Example 10

The catalyst A prepared in Example 1 was used for performing a low-carbon hydrocarbon aromatization reaction, the specific operations were as follows:

(1) a fixed bed reactor was used, and 1 g catalyst A was filled into a quartz reactor (with an inner diameter of 9 mm);

(2) $H_2$ was introduced into the reactor at a flow rate of 66.7 sccm and the reactor was heated to 630° C. at a temperature rise rate of 15° C./min, and the temperature was maintained for 30 min to perform preheating;

(3) the pressure was 0.02 MPa in terms of gauge pressure, the volume hourly space velocity (VHSV) was 0.75 $h^{-1}$, the $H_2$ with a flow rate of 66.7 sccm in step (2) was replaced with a mixture of three gases consisting of ethylene/$H_2$/$N_2$ ($N_2$ was used as an internal standard substance for chromatographic analysis) having a volume ratio of 1:1:1, after the reaction was carried out for 10 minutes, the products were analyzed by on-line gas chromatography for every 35 minutes, an average value of 12 hours was taken, the ethylene conversion rate, BTX selectivity, BTX yield, methane selectivity and ethane selectivity were subsequently calculated and obtained through the above test methods (Formula 1 to Formula 3), and the results were shown in Table 2.

After 12 hours of operation, the reaction was stopped, and the content of coke on the spent catalyst was measured with the following method: 10 mg of spent catalyst was weighted, the spent catalyst was placed in an alumina sample tray, the alumina sample tray was then disposed in a DTG-60H thermogravimetric analyzer produced by Shimadzu Corporation, the catalyst was heated to 800° C. at a temperature rise rate of 5° C./min in an air atmosphere. The coke content was quantified based on the weight loss between 400° C. and 650° C., and the results were shown in Table 2.

Example 11

The catalyst A of Example 10 after reaction for 12 hours was subjected to the regeneration treatment, the specific operations were as follows: the spent catalyst was heated to 550° C. at a temperature rise rate of 2° C./min in an air atmosphere and the temperature was maintained for 4 hours. The obtained aromatization catalyst was labeled as catalyst RA. Wherein the aromatization catalyst comprises a microporous material and a binder, the mol ratio of aluminum element to phosphorus element in the binder is 2; the weight ratio of the microporous material to the binder is 1:0.07, wherein the weight of said binder is calculated in terms of the aluminum element therein.

The catalyst RA was tested according to the aforementioned acidic site characterization method in the Test Examples, and the results were shown in Table 1.

Examples 12 to 20

The catalysts were prepared according to the same process as the Example 10, except that the catalyst A was replaced with catalysts B-I and RA, and the results were shown in Table 2.

Comparative Examples 11 to 15

The catalysts were prepared according to the same process as the Example 10, except that the catalyst A was replaced with catalysts D1-D5, and the results were shown in Table 2.

TABLE 2

| Catalysts | Ethylene conversion rate, % | BTX selectivity, % | BTX yield, % | $CH_4$ selectivity, % | $C_2H_6$ selectivity, % | Coke content, wt % |
|---|---|---|---|---|---|---|
| A | 84 | 62.2 | 52.3 | 12.6 | 12.3 | 1.86 |
| B | 80 | 65.1 | 52.1 | 11.2 | 10.5 | 1.23 |
| C | 91 | 59.3 | 54.0 | 13.9 | 11.5 | 3.01 |
| D | 86 | 66.6 | 57.4 | 12.7 | 9.7 | 1.61 |
| E | 81 | 66 | 53.5 | 11.1 | 10.5 | 1.35 |
| F | 82 | 65.3 | 53.5 | 12.5 | 10.4 | 1.42 |
| G | 94 | 45.6 | 42.8 | 6.0 | 40.4 | 6.32 |
| H | 93 | 46.1 | 42.9 | 5.9 | 39.8 | 5.9 |
| I | 91 | 48.2 | 43.4 | 7.8 | 37.2 | 5.8 |
| RA | 85 | 67 | 57.0 | 12.2 | 8.7 | 1.65 |
| D1 | 81 | 55.8 | 46.5 | 10.2 | 11.8 | 20.6 |
| D2 | 87 | 57 | 49.5 | 11.5 | 12.5 | 15.3 |
| D3 | 38 | 25 | 9.5 | 5.7 | 20 | 0.49 |
| D4 | 86 | 68.6 | 58.8 | 12.4 | 6.6 | 10.1 |
| D5 | 35 | 28 | 9.8 | 7.5 | 15.2 | 0.85 |

Example 21

The catalyst A of the present disclosure was subjected to the low-carbon olefin aromatization reaction at different temperatures:

(1) a fixed bed reactor was used, and 1 g catalyst A was filled into a quartz reactor (with an inner diameter of 9 mm);

$H_2$ was introduced into the reactor at a flow rate of 66.7 sccm and the reactor was heated to 630° C. at a temperature rise rate of 15° C./min, and the temperature was maintained for 30 min, then the reactor was cooled to 400° C. and the temperature was kept for 30 min;

(3) the pressure was 0.02 MPa in terms of gauge pressure, the volume hourly space velocity (VHSV) was 0.75 h$^{-1}$, the $H_2$ with a flow rate of 66.7 sccm in step (2) was replaced with ethylene having a flow rate of 10 sccm, $H_2$ having a flow rate of 10 sccm and $N_2$ having a flow rate of 10 sccm ($N_2$ was used as an internal standard substance for chromatographic analysis), after reaction at a temperature of 400° C. for 60 minutes, the temperature was then raised to 450° C., 500° C., 550° C., 600° C. and 630° C. in sequence, and the reaction was further performed for one hour at 450° C., 500° C., 550° C., 600° C. and 630° C. respectively; the gas was switched to $H_2$ having a flow rate of 66.7 sccm to purge for 30 minutes before each temperature rise, and after raising the temperature to the desired temperature, the hydrogen was then switched to the reaction gas (ethylene having a flow rate of 10 sccm, $H_2$ having a flow rate of 10 sccm and $N_2$ having a flow rate of 10 sccm, wherein $N_2$ was used as an internal standard substance for chromatographic analysis).

The products were analyzed for every 30 minutes with an on-line gas chromatography at 450° C., 500° C., 550° C., 600° C. and 630° C. respectively, the average value of 60 minutes was taken, the ethylene conversion rate, BTX selectivity, BTX yield, methane selectivity, and ethane selectivity were calculated and obtained through the above test methods. The results were shown in Table 3.

TABLE 3

| Reaction temperature, ° C. | Ethylene conversion rate, % | BTX selectivity, % | BTX yield, % | $CH_4$ selectivity, % | $C_2H_6$ selectivity, % |
|---|---|---|---|---|---|
| 400 | 98 | 30.1 | 29.5 | 0.4 | 2.4 |
| 450 | 97 | 36.2 | 34.9 | 1.4 | 4.0 |
| 500 | 93 | 43.6 | 40.7 | 4.5 | 6.1 |
| 550 | 89 | 54.5 | 48.5 | 8.6 | 8.1 |
| 600 | 86 | 61.6 | 52.8 | 11 | 9.9 |
| 630 | 85 | 63.7 | 54 | 11.8 | 11.6 |

As shown in the results of Table 1, the process of the present disclosure can be used for effectively adjusting the acidity of the strongly acidic sites/weakly acidic sites of the catalyst, the prepared aromatization catalysts may have a ratio of the acidity of the strongly acidic sites to the acidity of the weakly acidic sites of the olefin aromatization catalyst less than 1, preferably not more than 0.75.

The results of Table 2 demonstrate that the aromatization catalysts of the present disclosure can promote aromatization reaction of the low-carbon olefins to produce aromatic hydrocarbons, and the reaction temperature is low; in contrast to the Comparative Examples (phosphorus-containing solution is not added in the Comparative Example 1; the molar ratios of aluminum to phosphorus in the binder of the Comparative Examples 2 and 3 do not fall into the scope of the present disclosure, Comparative Example 4 discloses that only a hydrothermal treatment is performed after the molding process; the Comparative Example 5 discloses that the ZSM-5 molecular sieve is initially reacted with the phosphoric acid aqueous solution, and alumina is then added), the aromatization catalysts of the present disclosure still result in the high ethylene conversion, BTX selectivity and BTX yield, and lower amounts of generated methane and coke at the temperature of 400° C.

Figure 2:
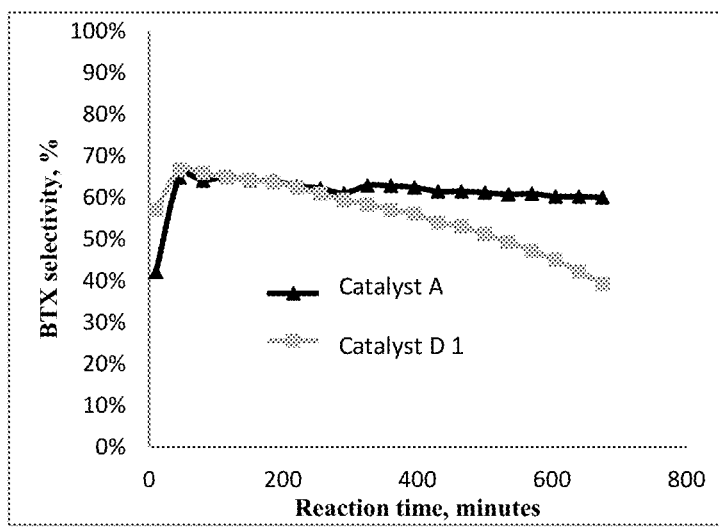
FIG. 2 illustrates a graph comparing the BTX selectivities of catalyst A of the present disclosure and catalyst D1 of the Comparative Example.

Furthermore, when the catalyst A of the present disclosure is compared with the catalyst D1 of the Comparative Example in terms of ethylene conversion rate and BTX selectivity, the comparison results are as shown in Table 2, FIG. 1 and FIG. 2, it can be seen from Table 2 that the catalyst A shows superior stability, it only contains 1.86 wt % of formed coke after the reaction for 12 hours, while the catalyst D1 includes a coke content more than 20 wt % after the reaction for 12 hours. Catalyst A also maintains a favorable BTX selectivity.

Figure 3:
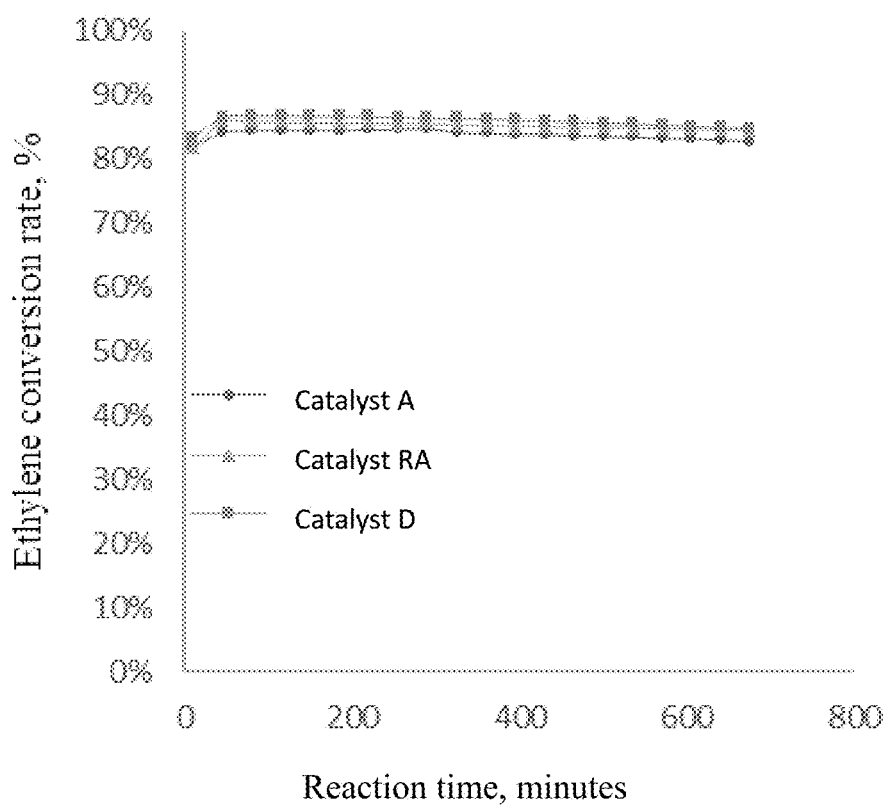
FIG. 3 illustrates a graph comparing the ethylene conversion rates of catalyst A, catalyst RA, and catalyst D of the present disclosure.
Figure 4:
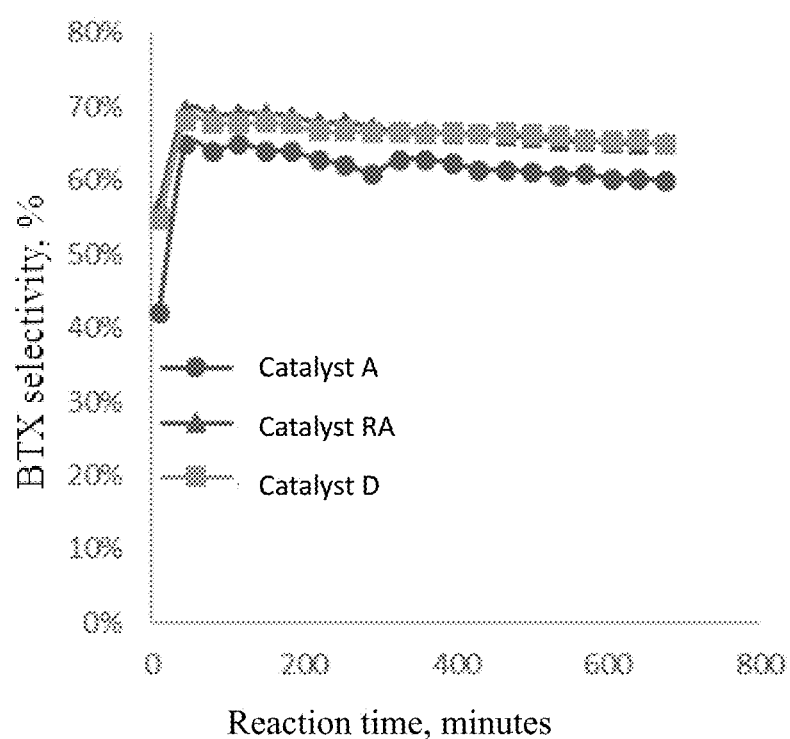
FIG. 4 illustrates a graph comparing the BTX selectivities of catalyst A, catalyst RA, and catalyst D of the present disclosure.

In addition, when comparing the catalyst A (the catalyst is a newly prepared product), the catalyst RA (obtained after regeneration of the catalyst A) and catalyst D (after catalyst A subjecting to a hydrothermal treatment) in terms of the ethylene conversion rate and BTX selectivity, the comparison results are shown in FIG. 3 and FIG. 4, it is illustrated that the activity and selectivity of the catalyst of the present disclosure are recoverable after the regeneration process, which indicates that the aromatization catalyst of the present disclosure has excellent hydrothermal stability and can be recycled, regenerated and reused for several times.

The results in Table 3 illustrate that the ethylene conversion rate more than 95% can be achieved at a temperatures as low as 400° C. The BTX selectivity at a lower temperature is relatively low, and most products are $C_3$-$C_6$, and the amount of generated methane is low.

To sum up, the aromatization catalyst of the present disclosure has shown excellent stability and desirable selectivity of aromatic hydrocarbon products, and can effectively reduce the generated amount of methane and coke in the process of subjecting low-carbon olefins to aromatization reaction to generate aromatic hydrocarbons.

The above content describes in detail the preferred embodiments of the present disclosure, but the present disclosure is not limited thereto. A variety of simple modifications can be made in regard to the technical solutions of the present disclosure within the scope of the technical concept of the present disclosure, including a combination of individual technical features in any other suitable manner, such simple modifications and combinations thereof shall also be regarded as the content disclosed by the present disclosure, each of them falls into the protection scope of the present disclosure.

The invention claimed is:

1. An olefin aromatization catalyst, comprising a microporous material, a binder and a modifier, wherein the microporous material is a zeolite molecular sieve, the binder comprises alumina, the modifier comprises phosphorus element, and a molar ratio of aluminum element in the binder to the phosphorus element is more than or equal to 1 and less than 5; the ratio of the acidity of the strongly acidic sites to the acidity of the weakly acidic sites of the olefin aromatization catalyst is less than 1; wherein the microporous material is a ZSM-5 molecular sieve.

2. The olefin aromatization catalyst of claim 1, wherein the ratio of the acidity of the strongly acidic sites to the acidity of the weakly acidic sites is not more than 0.85.

3. The olefin aromatization catalyst of claim 2, wherein the ratio of the acidity of the strongly acidic sites to the acidity of the weakly acidic sites is not more than 0.75.

4. The olefin aromatization catalyst of claim 1, wherein the weight ratio of the microporous material to the binder is 1:0.05-1, wherein the weight of said binder is calculated based on aluminum element therein.

5. The olefin aromatization catalyst of claim 1, wherein the ZSM-5 molecular sieve has a silica-alumina ratio not more than 50.

6. The olefin aromatization catalyst of claim 1, wherein at least a portion of the binder and the modifier in the catalyst is present in a form of aluminum phosphate.

7. The olefin aromatization catalyst of claim 1, wherein the aromatization catalyst further comprises above zero and up to 1 wt % of an active metal component based on the total amount of the aromatization catalyst, wherein the metal active component is one or more selected from the group consisting of Pt, Ni, Co, Cu, Zn, Fe, Pd, Rh, Ru, Re, Mo, W, Au and Ga.

8. A method for preparing the olefin aromatization catalyst of claim 1, comprising the following steps:
mixing the microporous material, an alumina precursor and a phosphorus source to form a mixture, molding and calcining the mixture; or
mixing the microporous material and an alumina precursor to form a mixture, molding and calcining the mixture, contacting the mixture with a phosphorus source to load the phosphorus element, subsequently carrying out a secondary calcination;
wherein the microporous material is a zeolite molecular sieve, the molar ratio of aluminum element in the alumina precursor to phosphorus element in the phosphorus source is more than 1 and less than 5, the temperatures of the calcination and secondary calcination are respectively within a range of 300° C.-700° C.; the times are respectively within a range of 0.5-24 hours, wherein the microporous material is a ZSM-5 molecular sieve.

9. The method of claim 8, wherein the temperatures of the calcination and secondary calcination are respectively within a range of 450° C.-600° C.; the times are respectively within a range of 2-8 hours.

10. The method of claim 8, wherein the weight ratio of the microporous material to the alumina precursor calculated in terms of aluminum element is 1:0.05-1.

11. The method of claim 8, wherein the ZSM-5 molecular sieve has a silica-alumina ratio not more than 50.

12. The method of claim 8, wherein the phosphorus source is a phosphorus-containing solution, and a loading mode is an impregnation method.

13. The method of claim 12, wherein a solute in the phosphorus-containing solution is one or more selected from the group consisting of phosphoric acid, ammonium phosphate, phosphine, and derivatives thereof.

14. The method of claim 8, further comprising subjecting a product obtained from calcination or a product obtained from the secondary calcination to a hydrothermal treatment; and the conditions of the hydrothermal treatment comprise: the temperature is within a range of 250-650° C., and the time is within a range of 0.5-24 h.

15. The method of claim 8, further comprising above zero and up to 1 wt % of an active metal component selected from the group consisting of Pt, Ni, Co, Cu, Zn, Fe, Pd, Rh, Ru, Re, Mo, W, Au and Ga; and/or further comprising loading above zero and up to 1 wt % of an active metal component on a product obtained from the calcination or a product obtained from the secondary calcination.

16. A low-carbon olefin aromatization process, comprising the following steps: contacting low-carbon olefin with hydrogen in the presence of a catalyst under aromatization conditions, wherein the catalyst is the aromatization catalyst of claim 1.

17. The process of claim 16, wherein the low-carbon olefin is $C_2$-$C_6$ olefin.

18. The process of claim 17, wherein the low-carbon olefin is ethylene.

19. The process of claim 16, wherein the aromatization conditions comprise: a pressure of 0.01 MPa-2 MPa in terms of the gauge pressure; a temperature within a range of 300° C.-700° C.; the volume ratio of hydrogen to the olefin of 0.1-5; the volume hourly space velocity (VHSV) of the low-carbon olefin of 500 $h^{-1}$ to 50,000 $h^{-1}$.

20. The process of claim 19, wherein the temperature is within a range of 500° C.-650° C.; the volume ratio of hydrogen to the olefin is 0.5-2; the volume hourly space velocity (VHSV) of the low-carbon olefin is 1,000 $h^{-1}$ to 10,000 $h^{-1}$.

21. The method of claim 12, wherein the phosphorus-containing solution has a content of phosphorus element within a range of from 0.5 wt % to 30 wt %.

22. The method of claim 12, wherein the phosphorus-containing solution has a content of phosphorus element within a range of from 5 wt % to 15 wt %.

* * * * *